United States Patent
Kasza

(10) Patent No.: US 6,244,052 B1
(45) Date of Patent: Jun. 12, 2001

(54) METHOD AND APPARATUS FOR PRODUCING PHASE CHANGE ICE PARTICULATE PERFLUOROCARBON SLURRIES

(75) Inventor: Kenneth E. Kasza, Palos Park, IL (US)

(73) Assignee: The University of Chicago, Chicago, IL (US)

( * ) Notice: Subject to any disclaimer, the term of this patent is extended or adjusted under 35 U.S.C. 154(b) by 0 days.

(21) Appl. No.: 09/585,770

(22) Filed: Jun. 2, 2000

Related U.S. Application Data

(60) Provisional application No. 60/146,753, filed on Aug. 2, 1999.

(51) Int. Cl.[7] .................................................. F25C 3/00
(52) U.S. Cl. ........................................ 62/1; 62/76; 62/330
(58) Field of Search ...................................... 62/1, 76, 330

(56) References Cited

U.S. PATENT DOCUMENTS

| | | | | |
|---|---|---|---|---|
| 2,800,456 | * | 7/1957 | Shepherd | 62/1 |
| 3,255,600 | * | 6/1966 | Mitchell et al. | 62/76 |
| 4,540,501 | * | 9/1985 | Ternes et al. | 62/1 |
| 4,838,039 | * | 6/1989 | Knodel | 62/330 |
| 5,065,598 | * | 11/1991 | Kurisu et al. | 62/330 |
| 5,218,828 | * | 6/1993 | Hino | 62/330 |
| 5,505,055 | * | 4/1996 | Franklin, Jr. | 62/330 |
| 6,012,298 | * | 1/2000 | Goldstein | 62/330 |

OTHER PUBLICATIONS

Copending provisional application by Kenneth E. Kasza et al., filed Aug. 2, 1999, provisional application No. 60/146,753 and entitled Method for Inducing Hypothermia.

* cited by examiner

Primary Examiner—William E. Tapolcai
(74) Attorney, Agent, or Firm—Joan Pennington

(57) ABSTRACT

A phase change ice particulate perfluorocarbon slurry and a method and apparatus are provided for producing phase change particulate perfluorocarbon slurries. A known amount of perfluorocarbon liquid is provided. A set percentage of a phase change liquid and optionally other additives, such as oxygen or other cell protectants are added to the known amount of perfluorocarbon liquid. The phase change liquid and the perfluorocarbon liquid are mixed to produce an emulsion of small droplets of the phase change liquid in the perfluorocarbon liquid. The emulsion is cooled to produce the phase change particulate perfluorocarbon slurry. A phase change ice particulate perfluorocarbon slurry comprises a known amount of perfluorocarbon liquid and a set percentage of a phase change liquid added to the known amount of perfluorocarbon liquid. An emulsion is formed by the set percentage of a phase change liquid and the known amount of perfluorocarbon liquid. The phase change particulate perfluorocarbon slurry is formed by cooling the emulsion to a freezing point. The phase change liquid includes water or a saline solution. A set percentage of water is provided in a range between about 5% and 50%. A set percentage of saline solution is provided in a range between about 0.5% and 6.0%.

20 Claims, 2 Drawing Sheets

METHOD AND APPARATUS FOR PRODUCING PHASE CHANGE ICE PARTICULATE PERFLUOROCARBON SLURRIES

This application claims the benefit of prior filed copending provisional application filed Aug. 2, 1999, by Kenneth E. Kasza et al., provisional application Ser. No. 60/146,753 and entitled METHOD FOR INDUCING HYPOTHERMIA. The subject matter of the above-identified copending provisional application is incorporated herein by reference.

CONTRACTUAL ORIGIN OF THE INVENTION

The United States Government has rights in this invention pursuant to Contract No. W-31-109-ENG-38 between the United States Government and Argonne National Laboratory.

FIELD OF THE INVENTION

The present invention relates to a method and apparatus for producing phase change ice particulate perfluorocarbon slurries of very high fluidity, cooling capacity and stability.

DESCRIPTION OF THE RELATED ART

Phase change slurries in the form of high concentrations of small ice particles in a liquid carrier have dramatically increased coolant capacity as compared to other liquids such as single phase water or other liquids involving no heat of fusion effects. Phase change ice slurries developed by the present inventor Kenneth F. Kasza have been used for cooling in large building complexes. The development of ice slurries by the inventor for cooling buildings has shown that ice particles suspended in water or other carrier liquid, if engineered to have the correct characteristics, can be pumped as readily as water and are stable for significant periods of time without agglomeration where ice particles freeze together or entangle in clusters. The cooling capacity of such a slurry can be 5 to 10 times, depending on the particular loading in the carrier liquid, that of an equal amount of water which exhibits only sensible heat cooling capacity. For use in cooling buildings, the particles preferably are small relative to the conduit diameter, not loaded to a level of more than 30% ice in order to enhance delivery to the target cooling zone, and relatively smooth to avoid particle entanglement and formation of large clusters. Small additions of certain types of chemicals, such as freezing point depressants, when added to a slurry during an appropriate time when making the slurry, have been shown to dramatically improve the fluidity and storability of the slurry by altering the microscale features (smoothing) of the individual particles comprising the slurry.

A need exists for an improved method and apparatus for producing phase change ice particulate perfluorocarbon slurries. It is desirable to produce phase change particulate perfluorocarbon slurries with high cooling capacity, fluidity, and stability, for example for use to induce targeted protective hypothermia of human organs/tissue during medical treatment.

It is an object of the present invention to provide a method and apparatus for producing phase change particulate perfluorocarbon slurries.

It is an object of the present invention to provide a phase change ice particulate perfluorocarbon slurry.

SUMMARY OF THE INVENTION

In brief, a phase change particulate perfluorocarbon slurry and a method and apparatus are provided for producing phase change particulate perfluorocarbon slurries. A known amount of perfluorocarbon liquid is provided. A set percentage of a phase change liquid is added to the known amount of perfluorocarbon liquid. The phase change liquid and the perfluorocarbon liquid are mixed to produce an emulsion of small droplets of the phase change liquid in the perfluorocarbon liquid. The emulsion is cooled to produce the phase change particulate perfluorocarbon slurry.

A phase change ice particulate perfluorocarbon slurry comprises a known amount of perfluorocarbon liquid and a set percentage of a phase change liquid added to the known amount of perfluorocarbon liquid. An emulsion is formed by the set percentage of a phase change liquid and the known amount of perfluorocarbon liquid. The phase change ice particulate perfluorocarbon slurry is formed by cooling the emulsion to a freezing point.

In accordance with features of the invention, the phase change liquid includes water or a saline solution. The phase change liquid is immiscible in the perfluorocarbon liquid and has a higher freezing point than the perfluorocarbon liquid. The phase change particulate perfluorocarbon slurry is formed by cooling the emulsion to a freezing point of the phase change liquid to produce the phase change ice particulate perfluorocarbon slurry. A set percentage of water is provided in a range between about 5% and 50%. A set percentage of saline solution is provided in a range between about 0.5% and 6.0%.

BRIEF DESCRIPTION OF THE DRAWINGS

The present invention together with the above and other objects and advantages may best be understood from the following detailed description of the preferred embodiments of the invention illustrated in the drawings, wherein.

DETAILED DESCRIPTION OF THE PREFERRED EMBODIMENTS

Figure 1:
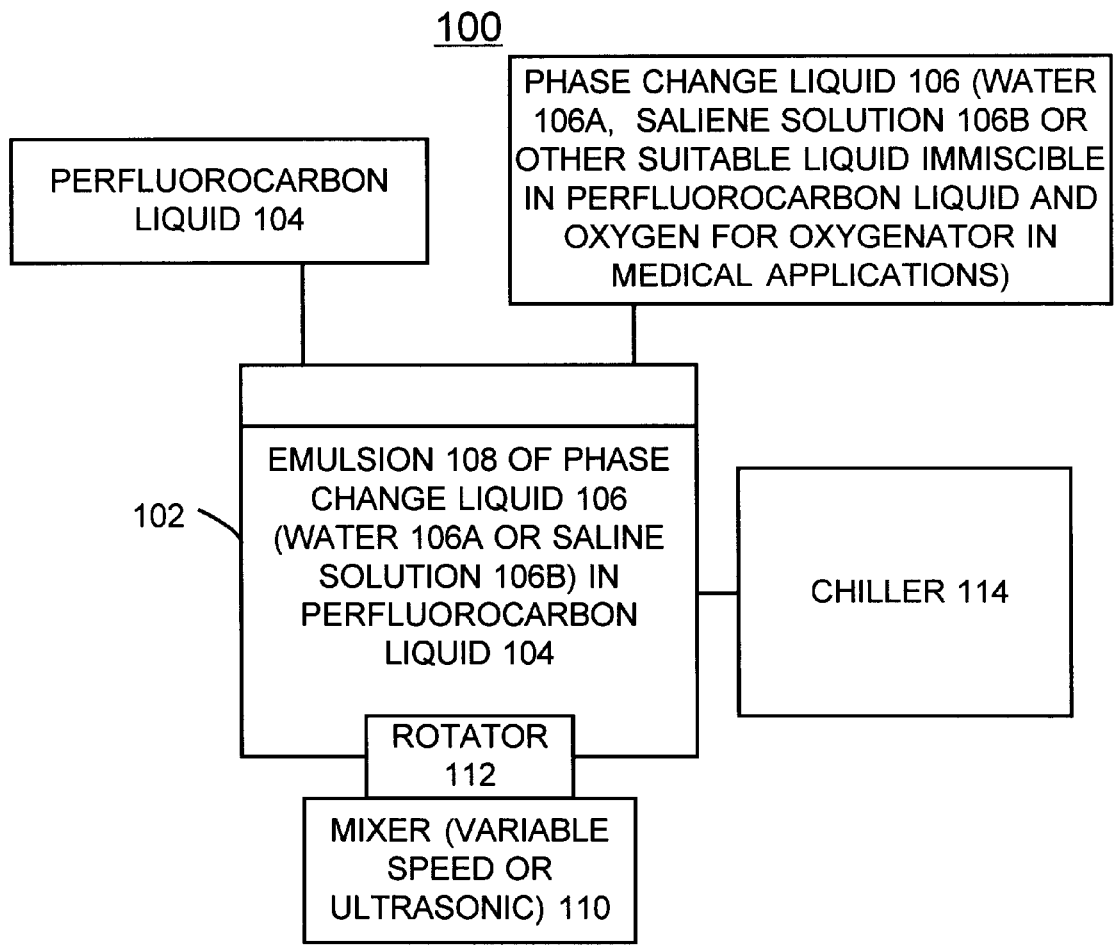
FIG. 1 is a block diagram representation illustrating exemplary apparatus for producing phase change particulate perfluorocarbon slurries in accordance with a preferred embodiment of the invention.

Having reference now to the drawings, in FIG. 1 there is shown apparatus for producing phase change particulate perfluorocarbon slurries in accordance with a preferred embodiment of the invention and generally designated by reference character 100. A container 102 is coupled to a source of a perfluorocarbon liquid 104 and a phase change liquid 106 and oxygen for medical applications. The phase change liquid 106 includes water 106A, a saline solution 106B or other suitable solution. The perfluorocarbon liquid 104 is immiscible with water, very chemically and biologically inert, and has an extraordinary capacity for dissolving oxygen. The phase change liquid 106 has a higher freezing point than the perfluorocarbon liquid 104 and the phase change liquid 106 is immiscible in the perfluorocarbon liquid 104.

An emulsion 108 is formed by intensely mixing a known amount of the perfluorocarbon liquid 104 with a set percentage of the phase change liquid 106, such as water 106A or saline solution 106B. A mixer 110, such as a variable speed mixer with a rotator 112 or an ultrasonic mixer, can be used to emulsify the phase change liquid 106 into the perfluorocarbon liquid 104. A selected mixer speed or energy level is selected together with a selected mixing duration to produce very small droplets of the phase change liquid 106 suspended in the immiscible perfluorocarbon liquid 104. The slurry fluidity or flowability depends on loading and the size and shape of the particles. Emulsion 108 is mixed to produce very small phase change liquid droplets having a generally globular or spherical shape. Then the ice particle perfluorocarbon liquid slurry is formed by cooling the emulsion 108 to the freezing point of the phase change liquid 106.

Emulsion 108 includes small, globular or spherical shaped droplets of water 106A, saline solution 106B, or other suitable liquid, and optionally oxygen entrained in perfluorocarbon liquid 104. Cooling is provided with, for example, a chiller 114 or other suitable device is used for cooling the emulsion 108. The container 102 with the emulsion 108 also can be batch cooled to the ice particle formation temperature by immersion in a recirculating bath chiller 114 or other suitable cooling device.

In accordance with features of the invention, phase change liquid (water) or ice particle loading is preferably in the range of about 5% to 50%. Saline solution concentrations are preferably in the range of about 0.5% to 6.0%. The phase change particulate perfluorocarbon slurry of the preferred embodiment is stable or storable, highly fluid and highly loaded ice particle medical grade slurry. A phase change particulate perfluorocarbon slurry of the preferred embodiment advantageously can be used for charging the lungs for cooling of the heart and for cooling other organs/tissue. The perfluorocarbon liquid slurry coolant also can serve as a liquid ventilator or oxygen transporter when the slurry is infused with oxygen. Other chemicals needed for maintaining cell viability can also be conveyed by the slurry to the desirable targets.

Figure 2:
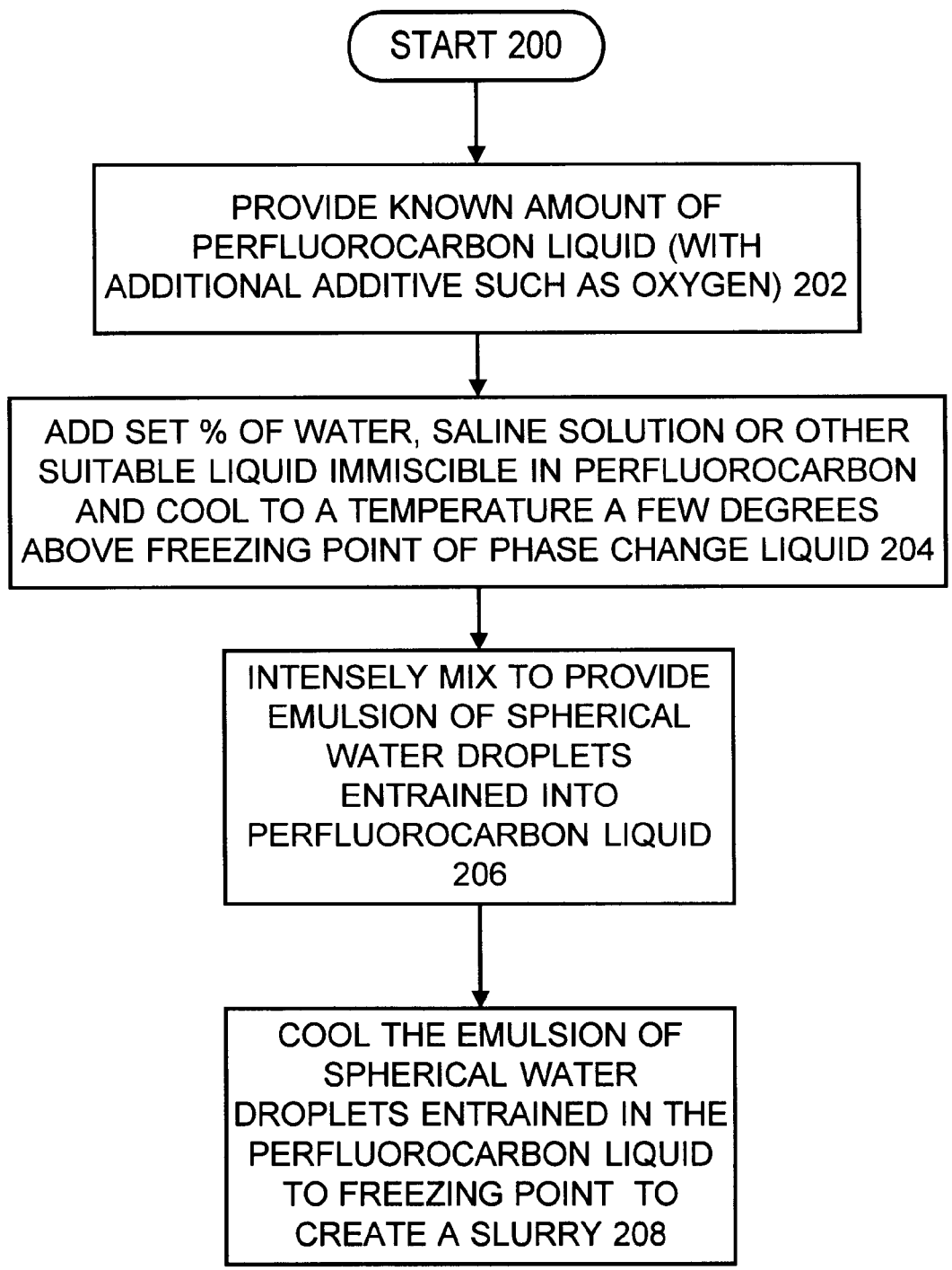
FIG. 2 is a flow chart illustrating exemplary steps for producing phase change particulate perfluorocarbon slurries in accordance with a preferred embodiment of the invention.

Referring to FIG. 2, there are shown exemplary steps for producing phase change particulate perfluorocarbon slurries in accordance with a preferred embodiment of the invention starting at a block 200. First a known amount of perfluorocarbon liquid is provided as indicated in a block 202. The perfluorocarbon liquid 104 optionally can include additional additive, such as oxygen when it is desired to use the slurry both as a coolant and a tissue/cell oxygenator for medical applications or with other cell beneficial chemicals. A set percentage of water 104A, saline solution 104B or other suitable solution that is immiscible in perfluorocarbon liquid is added and the liquids are cooled to a selected temperature a few degrees above the freezing point of the phase change liquid as indicated in a block 204.

With water, a set percentage in the range of about 5% to 50% is added. With saline solution, a set percentage in the range of about 0.5% to 6.0% is added. An emulsion of small spherical water or saline solution droplets entrained into the perfluorocarbon liquid is provided by combining the liquids, for example, by intensely mixing the liquids as indicated in a block 206. The size of the water, saline solution or other phase change liquid droplets prior to freezing determines the slurry ice particle size after freezing. The formation of small smooth ice particles enhances slurry flowability.

Mixing the liquids at block 206 can be provided by mechanically mixing the constituents in container 102 with a variable speed mixer. The more intense and longer the duration of the mixing provides smaller droplets. An ultrasonic mixer can be used to achieve small water or saline solution droplet sizes. The ultrasonic mixer allows the use of closed sterilized containers of the desired mixture processed for particle size without concerns of contamination. The mixing energy is transferred through the walls of the container. Next the container of the mixed solutions is batch cooled, for example, by immersion in a recirculating bath chiller, to the ice particle formation temperature of the phase change liquid to create a slurry as indicated in a block 208. The slurry can also be made in a continuous process device for on-demand delivery.

While the present invention has been described with reference to the details of the embodiments of the invention shown in the drawing, these details are not intended to limit the scope of the invention as claimed in the appended claims.

What is claimed is:

1. A method for producing phase change ice particulate perfluorocarbon slurries comprising the steps of:

providing a known amount of perfluorocarbon liquid;

adding a set percentage of a phase change liquid to said known amount of perfluorocarbon liquid;

mixing said phase change liquid and said perfluorocarbon liquid to produce an emulsion of small droplets of said phase change liquid in said perfluorocarbon liquid; and cooling said emulsion to produce the phase change particulate perfluorocarbon slurry.

2. A method for producing phase change ice particulate perfluorocarbon slurries as recited in claim 1 further includes the step, responsive to adding said set percentage of a phase change liquid to said known amount of perfluorocarbon liquid of cooling said perfluorocarbon liquid and said phase change liquid to a set temperature; said set temperature being a temperature above a freezing point of said perfluorocarbon liquid and said phase change liquid and wherein the step of cooling said emulsion to produce the phase change particulate perfluorocarbon slurry includes the step of cooling said emulsion to a freezing point of said phase change liquid to produce the phase change particulate perfluorocarbon slurry; said phase change liquid having a higher freezing point than said perfluorocarbon liquid and said phase change liquid being immiscible in said perfluorocarbon liquid.

3. A method for producing phase change ice particulate perfluorocarbon slurries as recited in claim 1 wherein the step of adding a set percentage of a phase change liquid to said known amount of perfluorocarbon liquid includes the step of adding a set percentage of water to said known amount of perfluorocarbon liquid.

4. A method for producing phase change ice particulate perfluorocarbon slurries as recited in claim 3 wherein the step of adding a set percentage of water to said known amount of perfluorocarbon liquid includes the step of adding said set percentage of water in a range between about 5% and 50%.

5. A method for producing phase change ice particulate perfluorocarbon slurries as recited in claim 1 wherein the step of adding a set percentage of a phase change liquid to said known amount of perfluorocarbon liquid includes the step of adding a set percentage of a saline solution to said known amount of perfluorocarbon liquid.

6. A method for producing phase change ice particulate perfluorocarbon slurries as recited in claim 5 wherein the step of a set percentage of a saline solution to said known amount of perfluorocarbon liquid includes the step of adding said set percentage of saline solution in a range between about 0.5% and 6.0%.

7. A method for producing phase change ice particulate perfluorocarbon slurries as recited in claim 1 wherein the step of mixing said phase change liquid and said perfluorocarbon liquid to produce an emulsion of small droplets of said phase change liquid in said perfluorocarbon liquid includes the steps of utilizing a variable speed mixer and providing a selected mixer speed and a selected mixing duration to produce said small droplets of said phase change liquid in said perfluorocarbon liquid.

8. A method for producing phase change ice particulate perfluorocarbon slurries as recited in claim 1 wherein the step of mixing said phase change liquid and said perfluorocarbon liquid to produce an emulsion of small droplets of said phase change liquid in said perfluorocarbon liquid includes the step of utilizing an ultrasonic mixer and providing a selected mixer energy and a selected mixing duration to produce said small droplets of said phase change liquid in said perfluorocarbon liquid.

9. A method for producing phase change ice particulate perfluorocarbon slurries as recited in claim 1 wherein the step of cooling said emulsion to produce the phase change particulate perfluorocarbon slurry include the step of batch cooling by immersion in a recirculating bath chiller.

10. A phase change ice particulate perfluorocarbon slurry comprising:
    a known amount of perfluorocarbon liquid;
    a set percentage of a phase change liquid added to said known amount of perfluorocarbon liquid;
    an emulsion formed by said set percentage of a phase change liquid and said known amount of perfluorocarbon liquid; and
    the phase change particulate perfluorocarbon slurry formed by cooling said emulsion to a freezing point.

11. A phase change ice particulate perfluorocarbon slurry as recited in claim 10 wherein said phase change liquid comprises a set percentage of water added to said known amount of perfluorocarbon liquid.

12. A phase change ice particulate perfluorocarbon slurry as recited in claim 11 wherein said set percentage of water is provided in a range between about 5% and 50%.

13. A phase change ice particulate perfluorocarbon slurry as recited in claim 10 wherein said phase change liquid comprises a set percentage of saline solution added to said known amount of perfluorocarbon liquid.

14. A phase change ice particulate perfluorocarbon slurry as recited in claim 10 wherein said set percentage of saline solution is provided in a range between about 0.5% and 6.0%.

15. Apparatus for producing phase change particulate perfluorocarbon slurries comprising:
    means for providing a known amount of perfluorocarbon liquid;
    means for adding a set percentage of a phase change liquid to said known amount of perfluorocarbon liquid;
    means for mixing said phase change liquid and said perfluorocarbon liquid to produce an emulsion of small droplets of said phase change liquid in said perfluorocarbon liquid; and
    means for cooling said emulsion to produce the phase change solid particulate perfluorocarbon slurry.

16. Apparatus for producing phase change particulate perfluorocarbon slurries as recited in claim 15 wherein said means for mixing comprises one of a variable speed mixer and an ultrasonic mixer.

17. Apparatus for producing phase change particulate perfluorocarbon slurries as recited in claim 15 wherein said means for cooling includes a recirculating bath chiller.

18. A method for producing phase change particulate perfluorocarbon slurries comprising the steps of:
    emulsifying a set percentage of a phase change liquid into a known amount of perfluorocarbon liquid to produce an emulsion of small droplets of said phase change liquid in said perfluorocarbon liquid; and
    cooling said emulsion to produce the phase change particulate perfluorocarbon slurry.

19. A method for producing phase change particulate perfluorocarbon slurries as recited in claim 18 wherein said phase change liquid includes water and said set percentage of water is provided in a range between about 5% and 50%.

20. A method for producing phase change particulate perfluorocarbon slurries as recited in claim 18 wherein said phase change liquid includes a saline solution and said set percentage of saline solution is provided in a range between about 0.5% and 6.0%.

* * * * *